(12) United States Patent  
Ninomiya et al.

(10) Patent No.: US 10,500,410 B2  
(45) Date of Patent: Dec. 10, 2019

(54) LIGHT EMITTING BONE IMPLANTS

(71) Applicant: Cimphoni Life Sciences LLC, Delafield, WI (US)

(72) Inventors: James T. Ninomiya, Brookfield, WI (US); Janine A. Struve, Milwaukee, WI (US); Dorothee Weihrauch, West Allis, WI (US); Scott Howard Micoley, Plymouth, WI (US); Dale Selsor DiIulio, Suakville, WI (US); Douglas J. Birkholz, Madison, WI (US); Kyle Steven Jansson, Brookfield, WI (US); Richard B. Davidson, Oconomowoc, WI (US)

(73) Assignee: Cimphoni Life Sciences LLC, Delafield, WI (US)

( * ) Notice: Subject to any disclaimer, the term of this patent is extended or adjusted under 35 U.S.C. 154(b) by 178 days.

(21) Appl. No.: 15/444,121

(22) Filed: Feb. 27, 2017

(65) Prior Publication Data

US 2017/0319867 A1 Nov. 9, 2017

Related U.S. Application Data

(60) Provisional application No. 62/373,842, filed on Aug. 11, 2016, provisional application No. 62/300,305, filed on Feb. 26, 2016.

(51) Int. Cl.
*A61N 5/06* (2006.01)
*A61B 17/16* (2006.01)
(Continued)

(52) U.S. Cl.
CPC ........ *A61N 5/0601* (2013.01); *A61B 17/1668* (2013.01); *A61B 17/1721* (2013.01);
(Continued)

(58) Field of Classification Search
CPC ..... A61B 17/00; A61B 17/1725; A61B 17/17; A61B 8/00; A61B 17/7061; A61F 2/28;
(Continued)

(56) References Cited

U.S. PATENT DOCUMENTS

| 3,964,473 A * | 6/1976 | Wickham | A61B 17/58 |
| | | | 623/23.16 |
| 4,026,304 A * | 5/1977 | Levy | A61N 1/372 |
| | | | 607/51 |

(Continued)

FOREIGN PATENT DOCUMENTS

| CN | 1994235 A | 7/2007 |
| CN | 201029876 Y | 3/2008 |
| WO | WO 2003002201 A1 | 1/2003 |

OTHER PUBLICATIONS

International Search Report and Written Opinion for International Application No. PCT/US17/19756 dated Jun. 28, 2017, 11 pages.
(Continued)

*Primary Examiner* — Alvin J Stewart  
(74) *Attorney, Agent, or Firm* — Quarles & Brady LLP

(57) ABSTRACT

A bone implant includes a rod having an aperture extending entirely through the rod. The aperture is to receive a fastener to couple the rod to a bone of a patient. The bone implant also includes a light source disposed on the rod. The light source is to emit light onto a portion of the bone adjacent the rod to at least one of stimulate bone growth or reduce bone loss.

13 Claims, 9 Drawing Sheets

(51) Int. Cl.
  *A61B 17/17* (2006.01)
  *A61F 2/28* (2006.01)
  *A61B 17/68* (2006.01)
  *A61B 17/88* (2006.01)
  *A61N 5/10* (2006.01)
  *A61B 17/74* (2006.01)
  *A61B 17/86* (2006.01)
  *A61F 2/36* (2006.01)
  *A61F 2/48* (2006.01)

(52) U.S. Cl.
  CPC ........ *A61B 17/1742* (2013.01); *A61B 17/686* (2013.01); *A61B 17/742* (2013.01); *A61B 17/869* (2013.01); *A61B 17/8625* (2013.01); *A61B 17/88* (2013.01); *A61F 2/28* (2013.01); *A61N 5/0613* (2013.01); *A61N 5/1048* (2013.01); *A61B 17/86* (2013.01); *A61F 2/36* (2013.01); *A61F 2002/482* (2013.01); *A61N 2005/0612* (2013.01); *A61N 2005/0626* (2013.01); *A61N 2005/0651* (2013.01); *A61N 2005/0652* (2013.01); *A61N 2005/0653* (2013.01); *A61N 2005/0658* (2013.01); *A61N 2005/0659* (2013.01); *A61N 2005/0662* (2013.01); *A61N 2005/0663* (2013.01)

(58) Field of Classification Search
  CPC . A61F 2/36; A61N 5/0601; A61N 2005/0612; A61N 5/0613; A61N 2005/0629; A61N 2005/063; A61N 2005/065; A61N 1/326; A61N 1/36
  See application file for complete search history.

(56) References Cited

U.S. PATENT DOCUMENTS

| | | | | |
|---|---|---|---|---|
| 4,313,438 A * | 2/1982 | Greatbatch | A61B 17/58 | 604/891.1 |
| 4,314,554 A * | 2/1982 | Greatbatch | A61B 17/58 | 604/20 |
| 4,549,547 A * | 10/1985 | Brighton | A61N 1/3787 | 607/51 |
| 4,602,638 A * | 7/1986 | Adams | A61N 1/05 | 607/52 |
| 5,030,236 A * | 7/1991 | Dean | A61F 2/367 | 433/201.1 |
| 5,304,210 A * | 4/1994 | Crook | A61N 1/326 | 607/51 |
| 5,330,477 A * | 7/1994 | Crook | A61B 17/70 | 606/280 |
| 5,396,880 A * | 3/1995 | Kagan | A61B 1/0051 | 600/109 |
| 5,417,688 A * | 5/1995 | Elstrom | A61B 17/1703 | 601/3 |
| 5,441,527 A * | 8/1995 | Erickson | A61N 1/05 | 607/116 |
| 5,540,691 A * | 7/1996 | Elstrom | A61B 17/1703 | 606/64 |
| 5,565,005 A * | 10/1996 | Erickson | A61N 1/05 | 128/903 |
| 5,738,521 A * | 4/1998 | Dugot | A61C 8/0006 | 433/173 |
| 5,807,397 A * | 9/1998 | Barreras | A61N 1/37223 | 607/61 |
| 6,019,761 A | 2/2000 | Gustilo | | |
| 6,120,502 A * | 9/2000 | Michelson | A61B 17/1671 | 606/247 |
| 6,143,035 A * | 11/2000 | McDowell | A61B 17/68 | 607/50 |
| 6,270,492 B1 * | 8/2001 | Sinofsky | A61L 2/10 | 606/13 |
| 6,503,269 B2 * | 1/2003 | Nield | A61B 18/22 | 606/10 |
| 7,465,313 B2 * | 12/2008 | DiMauro | A61N 5/0601 | 128/898 |
| 8,145,319 B1 * | 3/2012 | Simon | A61N 1/326 | 607/51 |
| 9,327,115 B2 * | 5/2016 | Neuman | A61N 1/326 | |
| 2003/0225331 A1 | 12/2003 | Diederich | A61N 7/02 | 600/437 |
| 2004/0111132 A1 * | 6/2004 | Shenderova | A61N 5/0616 | 607/88 |
| 2004/0199219 A1 * | 10/2004 | Dodge | A61N 1/205 | 607/51 |
| 2005/0096655 A1 * | 5/2005 | Trinchese | A61B 17/1707 | 606/62 |
| 2005/0175658 A1 * | 8/2005 | DiMauro | A61F 2/30767 | 424/423 |
| 2006/0206209 A1 * | 9/2006 | Cragg | A61B 17/8811 | 623/17.16 |
| 2006/0265077 A1 * | 11/2006 | Zwirkoski | A61B 17/7094 | 623/17.16 |
| 2007/0073300 A1 * | 3/2007 | Attawia | A61B 17/86 | 606/328 |
| 2007/0100211 A1 * | 5/2007 | Selover | A61B 17/02 | 600/199 |
| 2007/0265682 A1 * | 11/2007 | Wiegmann | A61C 8/0007 | 607/51 |
| 2007/0270864 A1 * | 11/2007 | Gurtowski | A61B 5/0084 | 606/79 |
| 2008/0119421 A1 * | 5/2008 | Tuszynski | A61K 31/195 | 514/34 |
| 2008/0125784 A1 * | 5/2008 | Rabiner | A61B 17/68 | 606/92 |
| 2008/0154368 A1 * | 6/2008 | Justis | A61B 17/7013 | 623/11.11 |
| 2008/0154373 A1 * | 6/2008 | Protopsaltis | A61B 17/7013 | 623/17.12 |
| 2009/0143781 A1 * | 6/2009 | Mische | A61B 17/7225 | 606/63 |
| 2009/0177254 A1 * | 7/2009 | Boyden | A61L 2/0011 | 607/88 |
| 2011/0118740 A1 * | 5/2011 | Rabiner | A61B 17/7225 | 606/63 |
| 2012/0029638 A1 * | 2/2012 | Miller | A61F 2/44 | 623/17.12 |
| 2012/0041557 A1 * | 2/2012 | Frigg | A61B 17/686 | 623/16.11 |
| 2012/0109304 A1 * | 5/2012 | Balckwell | A61B 17/7061 | 623/17.12 |
| 2012/0129131 A1 * | 5/2012 | Baehre | A61B 17/00491 | 433/173 |
| 2012/0185016 A1 * | 7/2012 | Weiner | A61N 5/00 | 607/62 |
| 2012/0215281 A1 * | 8/2012 | Neuman | A61N 1/326 | 607/51 |
| 2012/0232407 A1 * | 9/2012 | Fisher | A61B 17/7032 | 600/477 |
| 2012/0277812 A1 * | 11/2012 | Kraus | A61B 17/86 | 606/86 R |
| 2014/0088367 A1 * | 3/2014 | DiMauro | A61B 17/025 | 600/202 |
| 2015/0148878 A1 * | 5/2015 | Yoo | A61N 1/0472 | 607/118 |
| 2016/0151639 A1 * | 6/2016 | Scharf | A61N 5/0601 | 607/92 |
| 2017/0245995 A1 * | 8/2017 | Ninomiya | A61F 2/28 | |
| 2017/0319867 A1 * | 11/2017 | Ninomiya | A61F 2/28 | |

OTHER PUBLICATIONS

International Search Report and Written Opinion for International Application No. PCT/US17/19759 dated Jul. 25, 2017, 11 pages.

* cited by examiner

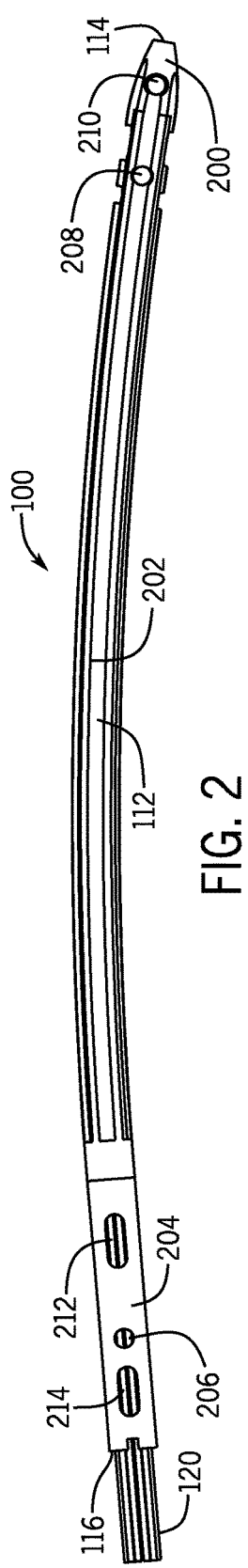
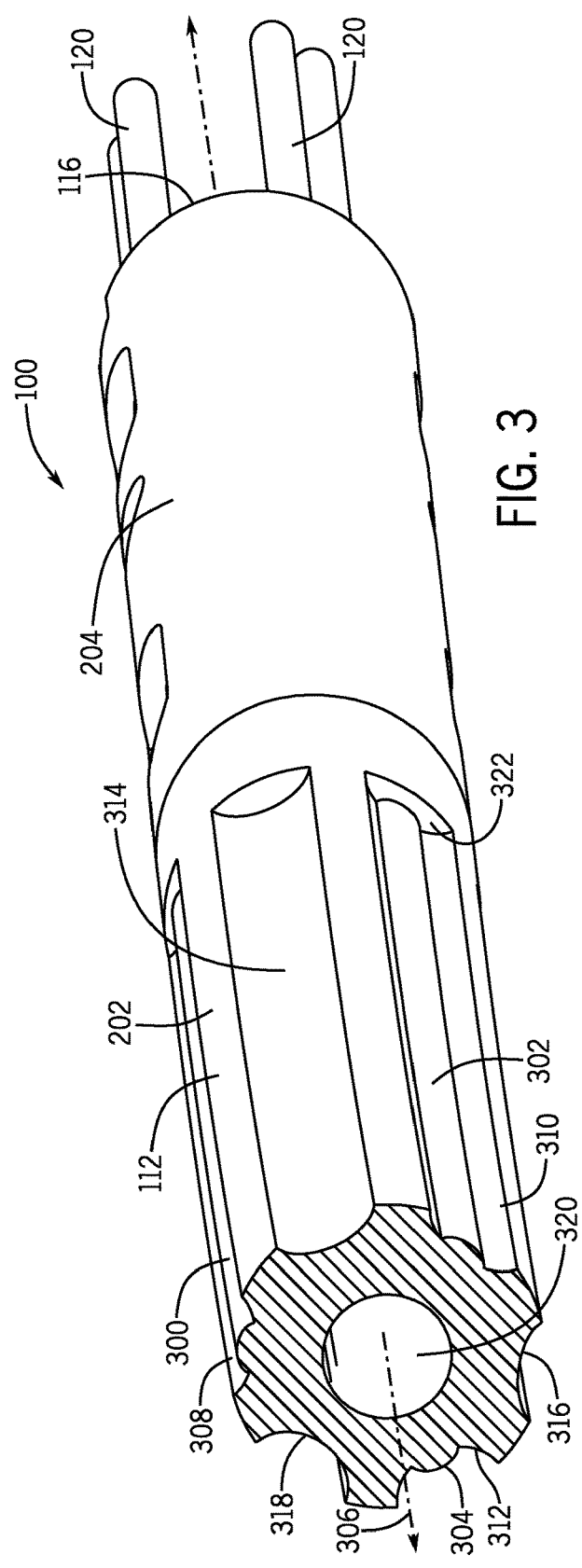

LIGHT EMITTING BONE IMPLANTS

RELATED APPLICATIONS

This application claims priority to U.S. Provisional Application No. 62/300,305, which is titled "Light Emitting Bone Implants" and was filed on Feb. 26, 2016. This application also claims priority to U.S. Provisional Application No. 62/373,842, which is titled "Light Emitting Bone Implants" and was filed on Aug. 11, 2016. Both U.S. Provisional Application No. 62/300,305 and U.S. Provisional Application No. 62/373,842 are incorporated by reference herein in their entireties.

BACKGROUND

Physicians routinely treat patients who have broken bones as a result of external trauma, which may occur during, for example, auto accidents, falls, worksite accidents, and war. Typically, surgeons implant rods or plates to secure and/or reinforce broken bones.

SUMMARY

In one embodiment of the invention, a bone implant includes a rod having an aperture extending entirely through the rod. The aperture is to receive a fastener to couple the rod to a bone of a patient. The bone implant also includes a light source disposed on the rod. The light source is to emit light onto a portion of the bone adjacent the rod to at least one of stimulate bone growth or reduce bone loss.

In another embodiment of the invention, a bone implant includes a plate having an aperture extending entirely through the plate. The bone implant also includes a light source to be received in the aperture. The light source is to emit light onto bone adjacent the plate to at least one of stimulate bone growth or reduce bone loss.

In another embodiment of the invention, a bone implant includes a light source to emit light having wavelengths from about 600 nanometers to about 950 nanometers. The bone implant also includes a controller to be operatively coupled to the light source. The controller is to control power supplied to the light source to enable the light source to deliver a predetermined dose of light to a bone. The bone implant also includes an aperture extending through the bone implant. The aperture is to receive a fastener to secure the bone implant to the bone.

DESCRIPTION OF THE DRAWINGS

FIG. 2 is a side view of the bone implant of FIG. 1.

FIG. 3 is a perspective, cross-sectional view of the bone implant of FIGS. 1 and 2 along line 3-3 of FIG. 1.

FIG. 7A is a top view of an aperture of the bone implant of FIGS. 6-7.

DETAILED DESCRIPTION

Figure 1:
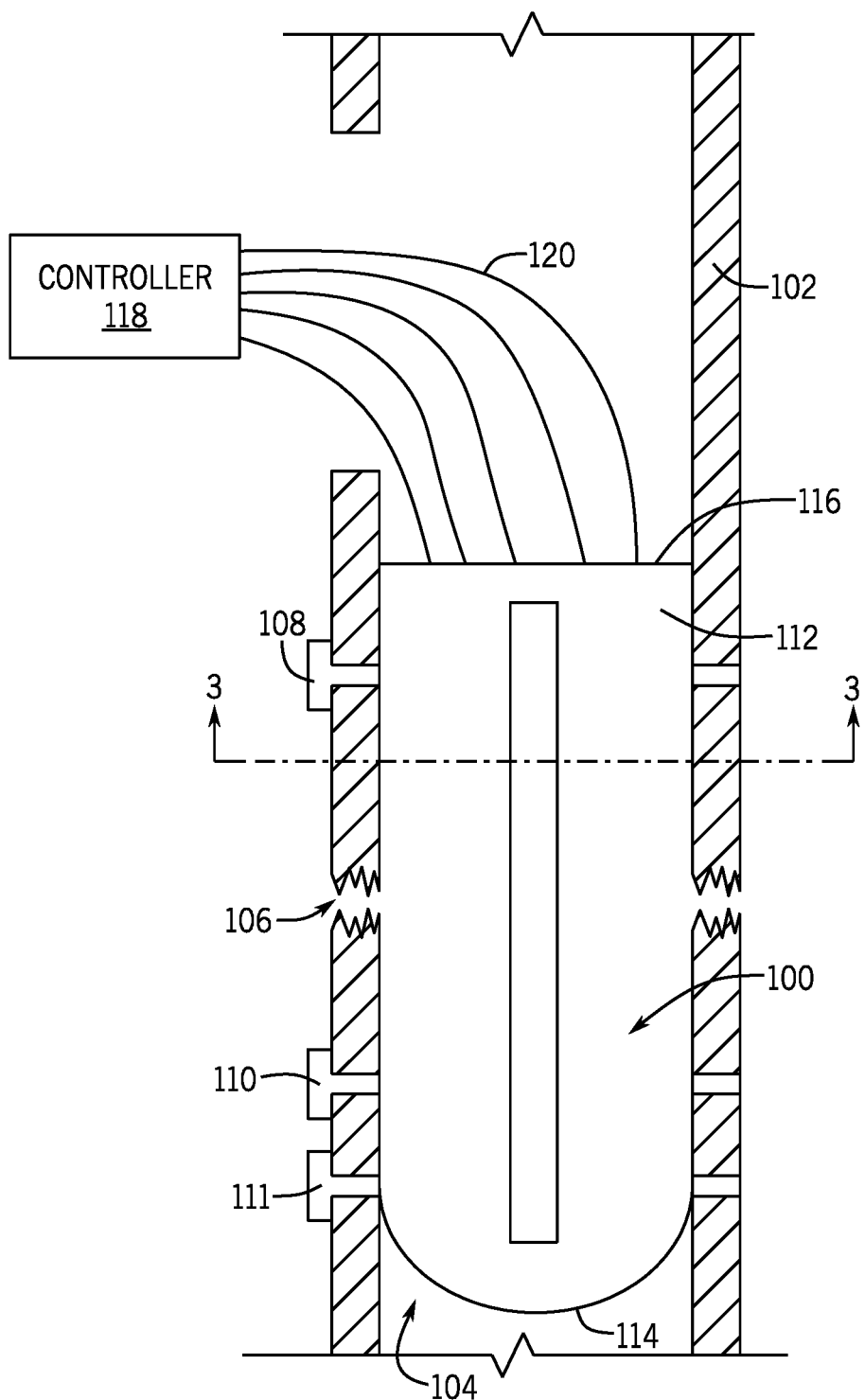
FIG. 1 is a schematic illustration of a bone implant positioned within a femur of a patient according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in the same or different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

The light emitting bone implants in some embodiments of the invention deliver predetermined doses of light to fractured bone to stimulate bone growth and, thus, healing of the bone. For example, a light emitting bone implant can be implanted into a bore of a fractured bone of a patient or onto an exterior of the bone. The bone implant includes one or more light sources, such as organic light emitting diodes that emit near infrared (NIR) light (e.g., light having wavelengths from about 600 nanometers to about 950 nanometers). In some embodiments, the light penetrates the bone by about one-sixteenth of an inch, decreasing osteoblast apoptosis and promoting cell proliferation of the bone. As a result, in some embodiments, an amount of time to heal a fractured bone can be halved relative to bone fractures secured via bone implants that do not emit near infrared light.

In some embodiments, the bone implant is operatively coupled to a controller, and the controller controls dosages (e.g., a duration of exposure at a predetermined irradiance level) and/or frequencies (e.g., duty cycle or time between exposures) at which the doses are delivered to the patient via the bone implant. For example, in some embodiments, the controller supplies power to the bone implant for a predetermined amount of time (e.g., thirty to sixty seconds) at predetermined times (e.g., once per day at noon, every twelve hours, etc.) to control an amount of light delivered to the patient. In some embodiments, the controller controls power to the bone implant so that the bone implant delivers about three to thirty Joules of energy per day. In some embodiments, the controller controls an amount of heat generated via the light emitting bone implant to prevent the light emitting bone implant from generating an amount of heat that damages or kills osteoblasts.

In some embodiments, the controller is disposed outside of the patient and is operatively coupled to the bone implant via leads extending from the bone implant and through skin of the patient to the controller. In some embodiments, the leads each include a frangible connection to enable the leads to be broken (i.e., severed) to decouple the controller from the bone implant. In other embodiments, the controller can be implanted in the patient.

FIG. 1 illustrates a bone implant 100 according to one embodiment of the invention. The bone implant 100 of FIG. 1 is surgically implanted into a femur 102 of a patient. Although the following description involves the femur 102, the bone implants disclosed herein may be implanted into other bones. The bone implant 100 is disposed in a bore or hollow portion 104 of the femur 102 and spans a fracture 106 of the femur 102. The bone implant 100 is secured to the femur 102 via a first fastener 108 (e.g., a screw, a bolt, and/or one or more additional and/or alternative fasteners), a second fastener 110 (e.g., a screw, a bolt, and/or one or more additional and/or alternative fasteners), and a third fastener 111 (e.g., a screw, a bolt, and/or one or more additional and/or alternative fasteners). As a result, the bone implant 100 holds the femur 102 together and/or prevents portions of the femur 102 from moving (e.g., sliding, rotating, etc.) relative to each other to facilitate healing of the fractured femur 102.

The bone implant 100 includes a rod 112 disposed entirely within the bore 104. The rod 112 includes a first or fore end 114 and a second or aft end 116. As described in greater detail below, the bone implant 100 emits light to expose the femur 102 to the light that stimulates bone growth to facilitate healing of the fracture 106. A controller 118 is operatively coupled to the bone implant 100. The controller 118 of FIG. 1 is disposed outside of the patient. In some embodiments, the controller 118 is disposed in or coupled to a garment worn by the patient. For example, the controller 118 may be disposed in a pouch strapped to the patient. The controller 118 controls a dosage of light delivered by the bone implant 100 and a frequency and/or schedule at which the bone implant 100 delivers a dose of the light. The controller 118 is operatively coupled to the bone implant 100 via six leads 120. In other embodiments, the controller 118 is operatively coupled to the bone implant 100 via other numbers of leads (e.g., 1, 2, 3, 4, 5, 7, . . . 10, etc.). The leads 120 extend from the aft end 116 of the rod 112 through the femur 102 and skin of the patient to the controller 118. In some embodiments, the controller 118 is coupled to the leads 120 via a coupling (e.g., a quick disconnect connector) that enables the patient to connect or disconnect the controller 120 from the leads 120. Thus, the patient may disconnect the controller 120 from the leads 120 and remove the garment including the controller 120 to, for example, enable the patient to bathe without the controller 120 being disposed on the patient. Then, after bathing, the patient may reconnect the controller 118 to the leads 120 via the coupling.

In other embodiments, the controller 118 is implantable in the patient. For example, the controller 118 can be implanted in subcutaneous tissue of the patient. In some such embodiments, the leads 120 may extend from the controller 118 through a subcutaneous tunnel (not shown) to electrically connect the leads 120 to the bone implant 100. In other embodiments, the bone implant 100 is operatively coupled to the controller 118 in one or more additional and/or alternative ways such as wirelessly via a wireless communications link.

Figure 1A:
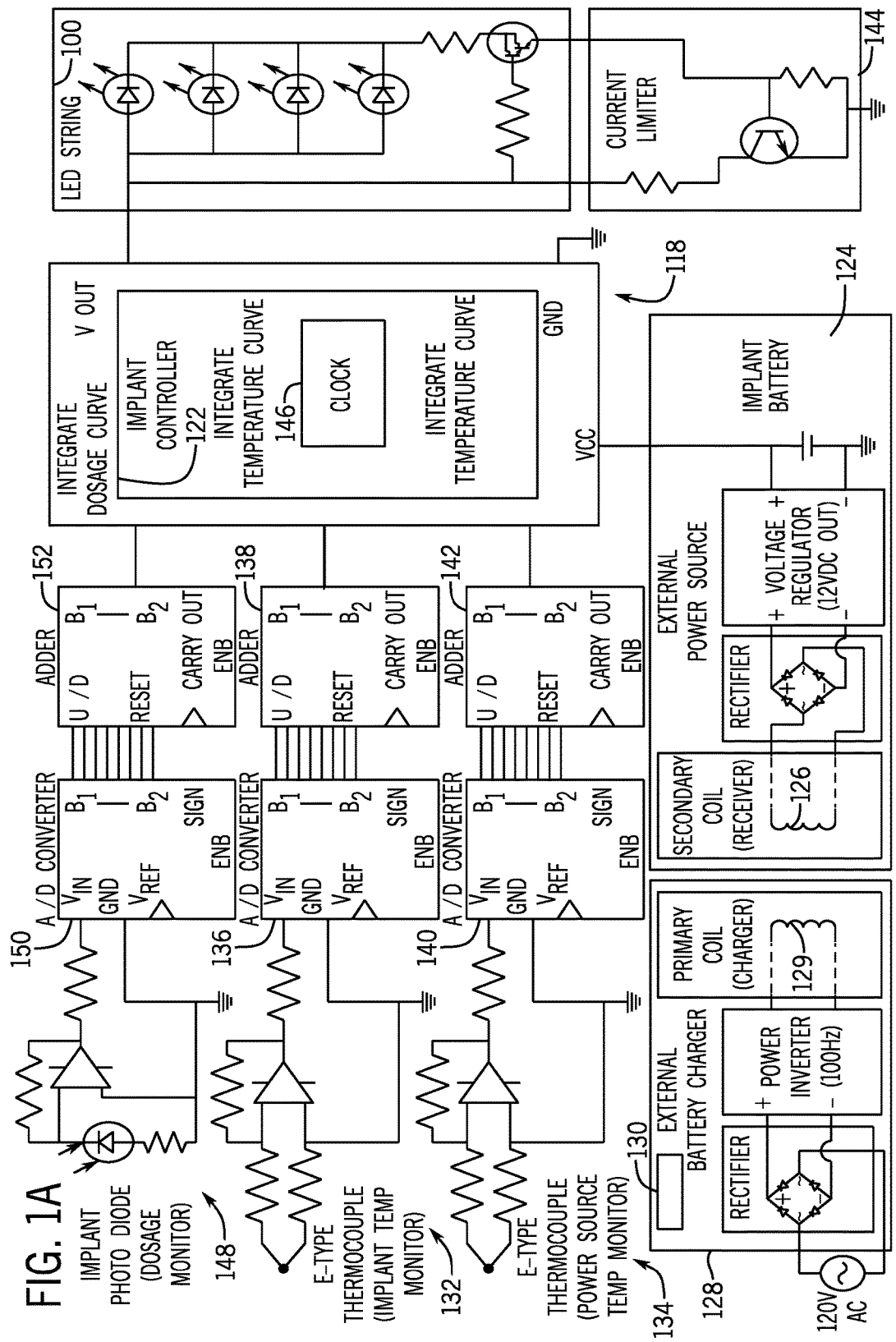
FIG. 1A is a schematic illustration of a controller operatively coupled to the bone implant of FIG. 1.

FIG. 1A is a schematic illustration of the controller 118 of FIG. 1. The controller 118 includes a processor 122 (e.g., a microprocessor) and a power source 124. The power source 124 supplies power to the bone implant 100 via the leads 120. In some embodiments, the power source 124 includes one or more rechargeable batteries such as, for example, a lithium-ion battery. In some embodiments, the one or more batteries has a capacity of about 3,000 milliamp-hours to about 4,000 milliamp-hours. The one or more rechargeable batteries may be housed in an inert housing (not shown).

In some embodiments, the power source 124 includes a first induction coil 126 to enable the power source 124 to be recharged via inductive charging. For example, the patient may employ a handheld device 128 that generates an alternating electromagnetic field via a second induction coil 129. When the patient positions the handheld device 128 in proximity of the power source 124, the first induction coil 126 of the power source 124 converts the alternating electromagnetic field to electric current. In other embodiments, the power source 124 may be charged or recharged via, for example, a 120 VAC to 12 VDC charger. In some embodiments, the handheld device 128 includes an output device 130 (e.g., a light, a speaker, etc.) to indicate that the handheld device 128 is positioned in proximity of the power source 124 to charge the power source 124. For example, if the handheld device 128 is positioned within about one inch of the power source 124, the handheld device 128 can illuminate a light on the handheld device 128 and/or generate a noise such as a beep to indicate that the handheld device 128 is positioned in proximity of the power source 124 to charge the power source 124.

In some embodiments, the controller 118 includes a first thermocouple 132 and a second thermocouple 134 (e.g., type E thermocouples) to determine an amount of heat generated by the bone implant 100 (e.g., during exposure of bone to light) and the power source 124 (during discharge or recharge), respectively. In some such embodiments, the controller 118 prevents the power source 124 from supplying power to the bone implant 100 if the controller 118 determines that the bone implant 100, the controller 118 and/or the power source 124 exceeds a first predetermined temperature (e.g., 38.5° C.) and/or if the bone implant 100, the controller 118, and/or the power source 124 is at or above a second predetermined temperature for a predetermined amount of time. For example, in the illustrated embodiment, the first thermocouple 132 includes a first analog-to-digital converter (ADC) 136 and a first adder 138. The first thermocouple 132 feeds a thermo-electric voltage from to the first ADC 136, and the first ADC 136 converts the voltage to a digital signal. The first adder 138 and an integrator of the processor 122 collect and integrate a change in temperature over time to determine if the first predetermined temperature of the bone implant 100 has been exceeded or if the bone implant 100 is at the second predetermined temperature for the predetermined amount of time. If the temperature of the bone implant 100 has exceeded the first predetermined temperature or is at the second predetermined temperature for the predetermined amount of time, the controller 118 discontinues operation of the bone implant 100 (e.g., stops supplying power to the bone implant 100).

In the illustrated embodiment, the second thermocouple 134 includes a second analog-to-digital converter (ADC) 140 and a second adder 142. The second thermocouple 134 feeds a thermo-electric voltage from to the second ADC 140, and the second ADC 140 converts the voltage to a digital signal. The second adder 142 and an integrator of the processor 122 collect and integrate a change in temperature over time to determine if the first predetermined temperature of the power source 124 has been exceeded or if the power source 124 is at or above the second predetermined temperature for the predetermined amount of time. If the temperature of the power source 124 has exceeded the predetermined temperature or is at or above the second predetermined temperature for the predetermined amount of time, the controller 118 discontinues operation of the power source 124 (e.g., stops recharging the power source 124).

In some embodiments, a current limiter and/or a shunt failsafe 144 is operatively coupled to the controller 118 to prevent the power source 124 from supplying current to the bone implant 100 if the controller 118 does not properly operate the bone implant 100 and/or if the power source 124 exceeds a predetermined rate of current flow during discharge or recharge of the power source 124 (e.g., 100 milliamps over sixty seconds, 500 milliamps over ten seconds, and/or any other predetermined rate).

In some embodiments, the processor 122 includes a clock 146 that the processor 122 employs to determine and/or monitor, for example, a time of day, a day of week, etc. The processor 122 controls times at which the power source 124 supplies power to the bone implant 100 and/or durations of time that the power source 124 supplies power to the bone implant 100 based on the clock 146. In some embodiments, the durations of time that the power source 124 supplies power to the bone implant 100 control dosages of light delivered by the bone implant 100. For example, in some embodiments, the processor 122 controls the power source 124 so that the power source 124 supplies power to the bone implant 100 for about thirty to about sixty seconds per day to enable the bone implant 100 to deliver a total of four Joules to six Joules of energy per day. For example, the processor 122 may control the power source 124 such that the bone implant 100 delivers a single dose of four Joules to six Joules of energy per day. In other embodiments, the processor 122 controls the power source 124 such that the bone implant 100 delivers more than one dose per day that sum to four to six Joules per day (e.g., five to ten second doses every four hours). In other embodiments, the processor 122 controls the power source 124 to enable the bone implant 100 to deliver different dosages of light (e.g., one Joule, five Joules, ten Joules, etc.) each day and/or at other frequencies (e.g., twice per day, three times per day, continuously, etc.).

In some embodiments, the controller 118 controls a dosage of light delivered via the bone implant 100 based on an amount of light emitted via the bone implant 100. For example, the controller 118 and/or the bone implant 100 can include a photodiode 148 that receives light emitted via the bone implant 100 and communicates a signal to the controller 118 indicative of an amount of light received by the photodiode 148. In some embodiments, the photodiode 148 is disposed on the bone implant 100 and receives light reflected from the femur 102. The photodiode 148 includes a third ADC converter 150 and a third adder 152. The photodiode 148 converts light into an analog current signal and feeds the analog current signal to a negative terminal of an Operational Amplifier. The Operational Amplifier amplifies the analog current signal and converts the analog current signal into a voltage. The third ADC 150 converts the voltage into a digital signal, and the third adder 152 and the processor 122 sum the digital signal over a period of time during which the bone implant 100 emits light. When the sum reaches a predetermined value corresponding to a dose of light (e.g., four to six Joules), the controller 118 disconnects the power source 124 from the bone implant 100 and resets the third adder 152 to zero.

Figure 1B:
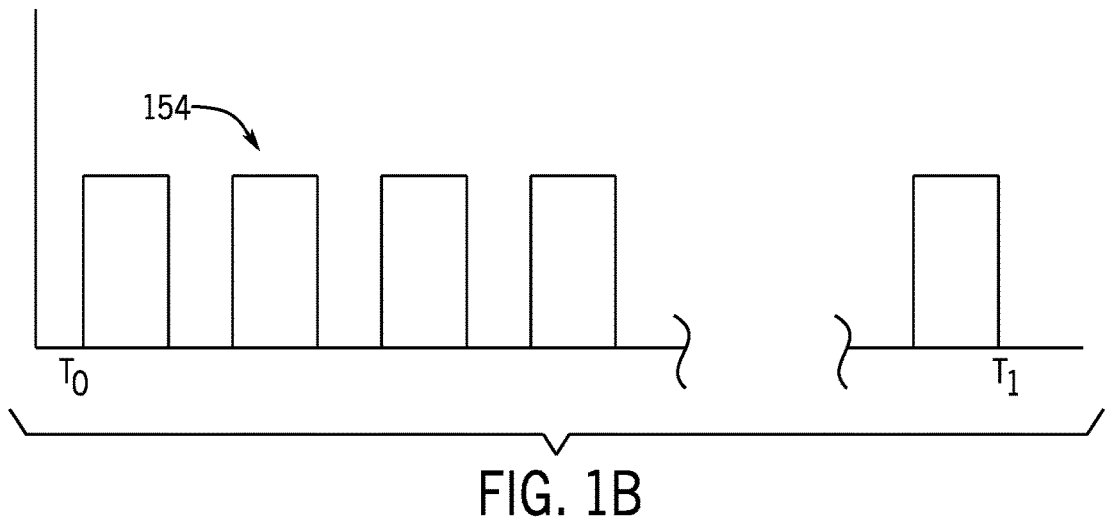
FIG. 1B is a graph of a waveform representative of power supplied to the bone implant of FIG. 1.

FIG. 1B is a graph illustrating a waveform 154 representative of power supplied via the controller 118 of FIG. 1A to the bone implant 100 of FIG. 1. The controller 118 employs pulse width modulation to control an amount of power supplied to the bone implant 100 from a first time $T_0$ to a second time $T_1$ to control a dosage of light delivered by the bone implant 100 to the femur 102. In some embodiments, the controller 118 controls the duty cycle of the power supplied to the bone implant 100 to enable the bone implant 100 to deliver a predetermined dosage of light to the femur 102. In one embodiment, the predetermined dosage of light is about four Joules.

Figure 1C:
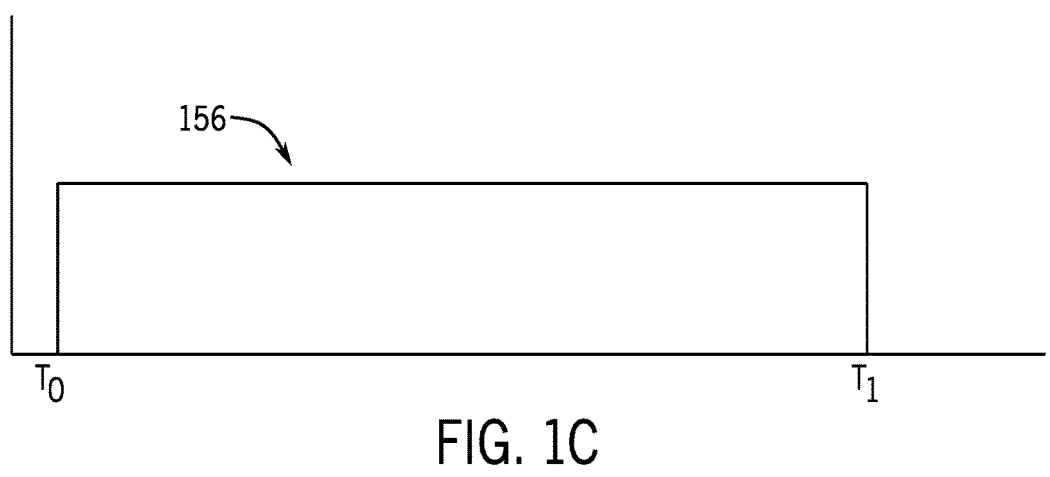
FIG. 1C is a graph of another waveform representative of power supplied to the bone implant of FIG. 1.

FIG. 1C is a graph illustrating an example waveform 156 representative of power supplied via the controller 118 of FIG. 1A to the bone implant 100 of FIG. 1. In the illustrated embodiment, the controller 118 supplies power continuously to the bone implant 100 from a first time $T_0$ to a second time $T_1$ so that the bone implant 100 delivers a predetermined dosage of light to the femur 102. In one embodiment, the predetermined dosage of light is about four Joules.

FIG. 2 is a side view of the bone implant 100 of FIG. 1. The rod 112 of the bone implant 100 includes a head 200, a base 202, and a tube 204. In the illustrated embodiment, the head 200 defines the fore end 114 of the rod 112, and the tube 204 defines the aft end 116. The base 202 is disposed between the head 200 and the tube 204. In some embodiments, the head 200, the base 202 and/or the tube 204 are constructed of one or more inert materials such as, for example, 316L stainless steel, titanium, cobalt chrome, molybdenum alloy, etc. The rod 112 may be a single piece or may be a plurality of pieces coupled together. For example, the tube 204 may be formed (e.g., molded, machined, etc.) separately from the base 202 and then coupled to the base 202 via, for example, threads. In the illustrated embodiment, the rod 112 is curved to have a curvature similar to or substantially the same as the femur 102. In other embodiments, the rod 112 is curved in other ways (e.g., to have a curvature similar to or substantially the same as a bone other than the femur 102).

In the illustrated embodiment, the rod 112 includes a first aperture 206, a second aperture 208, a third aperture 210, a first slot 212, and a second slot 214. The first aperture 206, the first slot 212, and the second slot 214 extend laterally or radially through the tube 204. The second aperture 208 extends laterally or radially through the base 202, and the third aperture 210 extends laterally or radially through the head 200. The first aperture 206, the second aperture 208, and the third aperture 210 receive the first fastener 108, the second fastener 110, and the third fastener 111, respectively, to secure the rod 112 to the femur 102. In some embodiments, the first slot 212 and the second slot 216 receive fasteners to secure the rod 112 to the femur 102 to prevent rotation of the rod 112. In other embodiments, the apertures 206, 208, 210 and/or the slots 212, 214 are configured in other ways (e.g., extend through different portions of the rod 112) and/or the rod 112 includes other numbers of apertures (e.g., 1, 2, 4, 5, etc.) and/or slots (e.g., 0, 1, 3, 4, etc.).

FIG. 3 is a perspective view of the bone implant 100 having a cross-section taken along line 3-3 of FIG. 1. The bone implant 100 includes a first light source 300, a second light source 302, and a third light source 304 that are each coupled to the base 202. For example, the first light source 300, the second light source 302, and the third light source 304 can be coupled to the base 202 via a conductive adhesive such as paste or glue. In some embodiments, the first light source 300, the second light source 302, and the third light source 304 are in contact with the base 202 to facilitate heat transfer from the first light source 300, the second light source 302, and the third light source 304 to the base 202. Thus, the base 202 can be a heat sink.

In some embodiments, the first light source 300, the second light source 302, and the third light source 304 are strips of light emitting diodes ("LED strips"). In some embodiments, the LED strips are organic LED strips. In some embodiments, the LED strips are thin, flexible strips having light emitting diodes connected in parallel. In some embodiments, each of the LED strips generates radiant power exposure of about 200 to about 250 milliwatts per square centimeter (mw/cm$^2$). In some embodiments, the LED strips each have a thickness of about two to three millimeters, a width of about six to ten millimeters, and a length substantially equal to a length of the base 202. In some embodiments, each of the LED strips has a viewing angle of about 120 degrees to about 170 degrees. In other embodiments, the first light source 300, the second light source 302, and the third light source 304 are implemented in one or more additional and/or alternative ways.

In some embodiments, the first light source 300, the second light source 302, and the third light source 304 emit near infrared (NIR) light (e.g., light having wavelengths from about 600 nanometers to about 950 nanometers). In some embodiments, the first light source 300, the second light source 302, and the third light source 304 emit light having wavelengths of about 670 nanometers. In some embodiments, the light penetrates the femur 102 by about one-sixteenth of an inch, decreasing osteoblast apoptosis and promoting cell proliferation of the femur 102. Although the bone implant 100 of FIG. 3 has three light sources, the bone implant 100 can include other numbers of light sources in other embodiments. For example, the bone implant 100 can include one light source, two light sources, five light sources, or other suitable numbers of individual or groups of light sources.

In some embodiments, the first light source 300, the second light source 302, and the third light source 304 extend substantially parallel to a central, longitudinal axis 306 of the rod 112. In other embodiments, the first light source 300, the second light source 302, and the third light source 304 are oriented in other ways. For example, the first light source 300, the second light source 302, and/or the third light source 304 can wrap around the base 202 substantially perpendicularly to the central, longitudinal axis 306 of the rod 112. In some embodiments, the first light source 300, the second light source 302, and/or the third light source 304 spiral around the base 202 (e.g., helically). The first light source 300, the second light source 302, and the third light source 304 emit light in a direction away from the central, longitudinal axis 306 of the rod 112.

In some embodiments, the bone implant 100 includes a cover (not shown) that covers the base 202 and the first light source 300, the second light source 302, and the third light source 304. In some embodiments, the cover prevents the first light source 300, the second light source 302, and the third light source 304 from coming into contact with bodily fluids during and after implantation of the bone implant 100. In one embodiment, the cover is transparent or clear. In other embodiments, the cover is translucent. In one embodiment, the cover is poly(methyl methacrylate) ("PMMA") overmolded to the base 202 and/or the first light source 300, the second light source 302, and the third light source 304. In some embodiments, the cover is a sleeve or tube, and the base 202 and the first light source 300, the second light source 302, and the third light source 304 are received in a receptacle of the sleeve.

In one embodiment, the base 202 includes a first groove or channel 308, a second groove or channel 310, and a third groove or channel 312 disposed equidistantly (e.g., about 120 degrees apart) about the central, longitudinal axis 306 of the rod 112. In the illustrated embodiment, the first light source 300, the second light source 302, and the third light source 304 are seated in the first channel 308, the second channel 310, and the third channel 312, respectively.

The base 202 also includes a fourth groove or channel 314, a fifth groove or channel 316, and a sixth groove or channel 318 disposed equidistantly (e.g., about 120 degrees) about the central, longitudinal axis 306 of the rod 112. In the illustrated embodiment, the channels 308, 310, 312, 314, 316, and 18 are equidistantly spaced apart from each other and, thus, are disposed symmetrically about the central, longitudinal axis 306. In some embodiments, the first light source 300, the second light source 302, and/or the third light source 304 are disposed in a respective one of the fourth channel 314, the fifth channel 316, and/or the sixth channel 318. In some embodiments, the rod 112 includes one or more additional light sources disposed in one or more of the fourth channel 314, the fifth channel 316, and the sixth channel 318.

In some embodiments, the rod 112 includes a passageway 320 that extends entirely through the rod 112 along the central, longitudinal axis 306. Thus, the passageway 320 provides a continuous opening from the fore end 114 to the aft end 116 of the rod 112. As a result, the passageway 314 enables the rod 112 to be inserted into the bore 104 of the femur 102 via a guide wire. In the illustrated embodiment, the passageway 320 has a circular cross-sectional shape taken substantially perpendicular to the central, longitudinal axis 306. In other embodiments, the passageway 320 may have other cross-sectional shapes.

In some embodiments, the first aperture 206, the second aperture 208, and the third aperture 210 are oriented to receive the first fastener 108, the second fastener 110, and the third fastener 111, respectively, to enable that the first fastener 108, the second fastener 110, and the third fastener 111 to extend substantially radially or laterally through the rod 112 (i.e., across the passageway 320 and intersecting the central, longitudinal axis 306). In some embodiments, the first slot 212 and the second slot 216 are oriented to receive one or more fasteners to enable the fasteners to extend substantially radially or laterally through the rod 112 (i.e., across the passageway 320 and intersecting the central, longitudinal axis 306).

In the illustrated embodiment, each of the light sources 300, 302, 304 is coupled to two of the leads 120. Although the following description involves the second light source 302 and the second channel 310, the following description is applicable to the first light source 300 and the first channel 308 and the third light source 304 and the third channel 312. Therefore, to avoid redundancy, separate descriptions of the first light source 300 and the third light source 304 are not separately set forth in this disclosure. The second light source 302 extends through an end wall 322 defining the second channel 310 to extend into the tube 204. Thus, two of the leads 120 are coupled to the second light source 302 within the tube 204. In other embodiments, two of the leads 120 extend through the end wall 322 into the second channel 316 and are coupled to the second light source 302 within the second channel 326.

Figure 4:
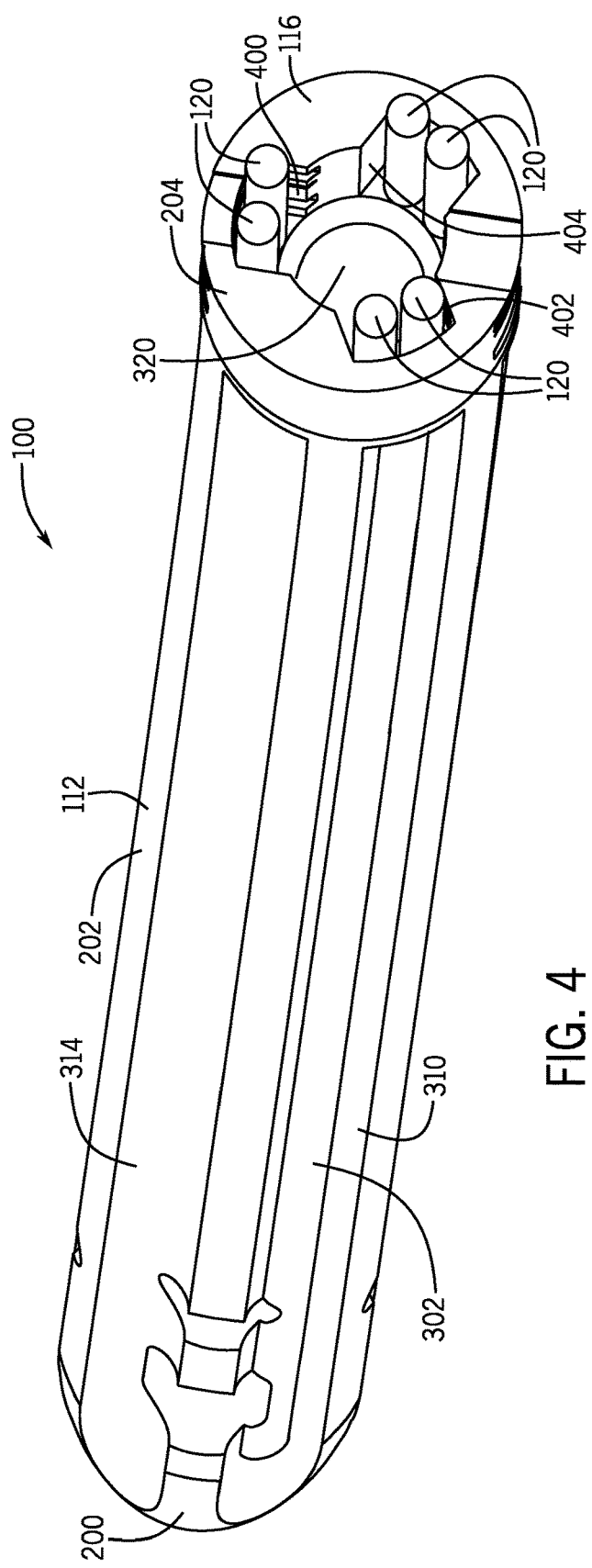
FIG. 4 is a perspective view of the bone implant of FIGS. 1 and 2-3.

FIG. 4 is a perspective view of the bone implant 100 illustrating the aft end 116 of the bore 112. In the illustrated embodiment, the tube 204 includes a first conduit 400, a second conduit 402, and a third conduit 404. Two of the leads 120 extend through the first conduit 400 to couple to the first light source 300, another two of the leads 120 extend through the second conduit 402 to couple to the second light source 302, and the other two of the leads 120 extend through the third conduit 404 to couple to the third light source 304. In the illustrated embodiment, the conduits 400, 402, 404 are disposed around the passageway 320 of the rod 112.

Figure 5:
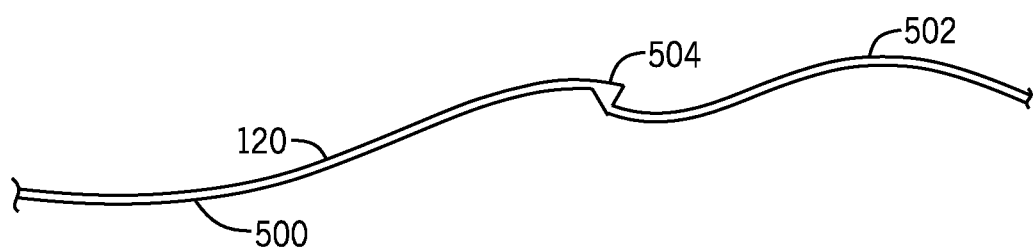
FIG. 5 illustrates a frangible lead operatively coupling the bone implant of FIGS. 1 and 2-3 to the controller of FIG. 1A.

FIG. 5 is a side view of one of the leads 120 of the bone implant 100 of FIGS. 1-4. Although only one of the leads 120 is described below, the following description is applicable to the other leads 120. In the illustrated embodiment, the lead 120 includes a first wire 500 and a second wire 502. The first wire 500 is coupled to the second wire 502 via a joint 504 (e.g., a spot weld). The first wire 500 extends from the joint 504 to the controller 118. The second wire 502 extends from the joint 504 to one of the light sources 300, 302, 304. The joint 504 is frangible. As a result, after the femur 102 heals, the controller 118 can be decoupled from the rod 112 by breaking or severing the joint 504. The joint 504 may be broken or severed by, for example, pulling and/or twisting the first wire 500. The first wire 500 may then be removed from the patient. After the controller 118 is decoupled from the bone implant 100, the bone implant 100 remains in the femur 102 to support and/or reinforce the femur 102.

Figure 6:
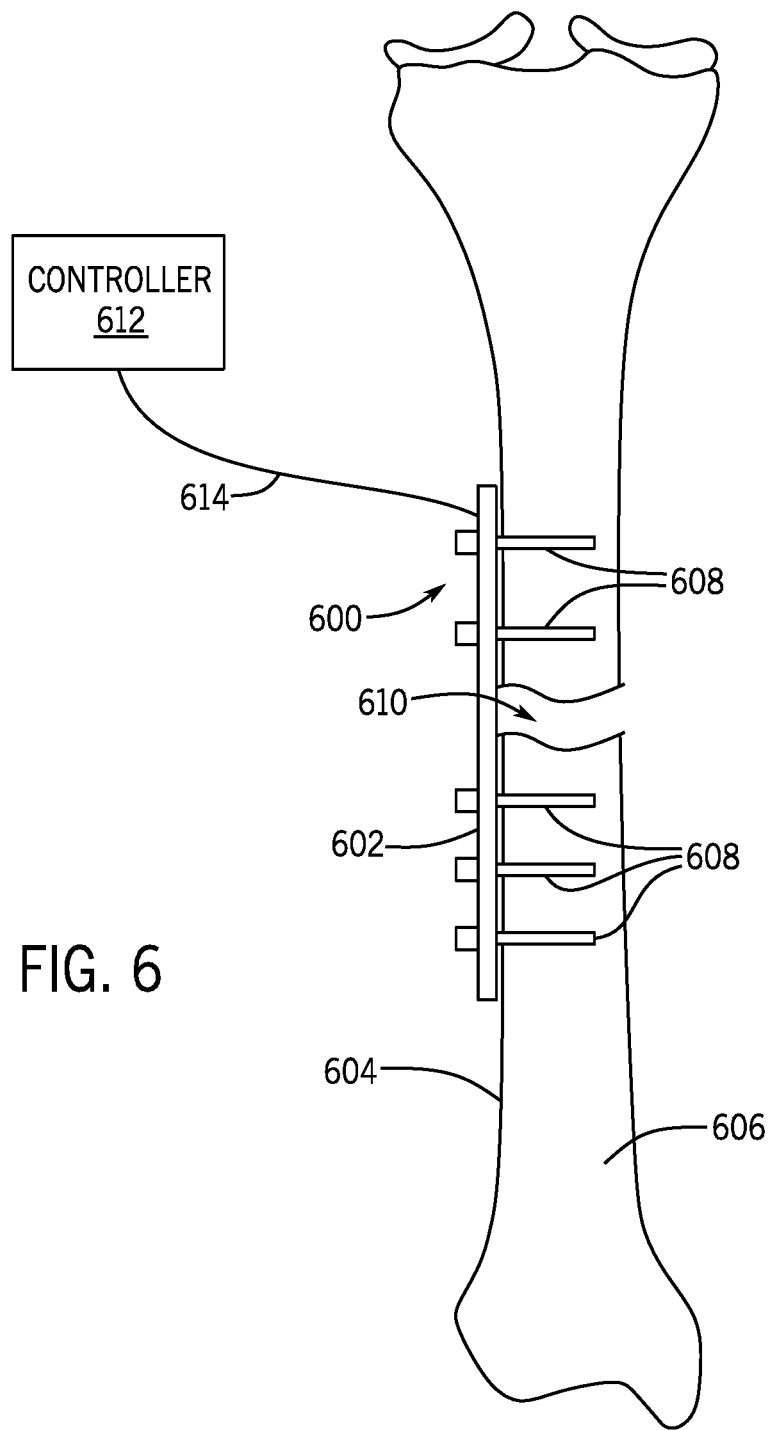
FIG. 6 is a schematic view of a bone implant according to yet another embodiment of the invention.

FIG. 6 illustrates another bone implant 600 disclosed herein. In the illustrated embodiment, the bone implant 600 includes a plate 602 secured to an exterior surface 604 of a bone 606 via a plurality of fasteners 608 (e.g., screws). The plate 602 spans a fracture 610 of the bone 606 to hold the bone 606 together and prevent portions of the bone 606 from moving (e.g., sliding, rotating, etc.) relative to each other to facilitate healing of the fractured bone 606. The bone implant 100 also emits light onto the bone 606 to stimulate bone growth to facilitate healing of the bone 606.

The bone implant 600 is operatively coupled to a controller 612. The controller 612 of FIG. 6 is disposed outside of the patient. The controller 612 controls a dosage of light delivered by the bone implant 600 and a frequency and/or schedule at which the bone implant 600 delivers a dose of the light. The controller 612 is operatively coupled to the bone implant 100 via leads 614. The leads 614 extend from the bone implant 600 through skin of the patient to the controller 612. In some embodiments, the leads 614 are frangible to enable the controller 612 to be decoupled from the bone implant 600. For example, the leads 614 may be implemented using the lead 120 of FIG. 5.

In other embodiments, the controller 612 is implantable in the patient. For example, the controller 612 can be implanted in subcutaneous tissue of the patient. In some such embodiments, the leads 614 may extend from the controller 612 through a subcutaneous tunnel (not shown) to electrically connect the leads 614 to the bone implant 600. In other embodiments, the bone implant 600 is operatively coupled to the controller 612 in one or more additional and/or alternative ways such as wirelessly via a wireless communications link. The controller 612 of FIG. 6 is identical to the controller 118 of FIG. 1A. Therefore, the description of the controller 118 of FIG. 1A is applicable to the controller 612 of FIG. 6. For the sake of avoiding redundancy, the controller 612 is not separately described herein.

Figure 7:
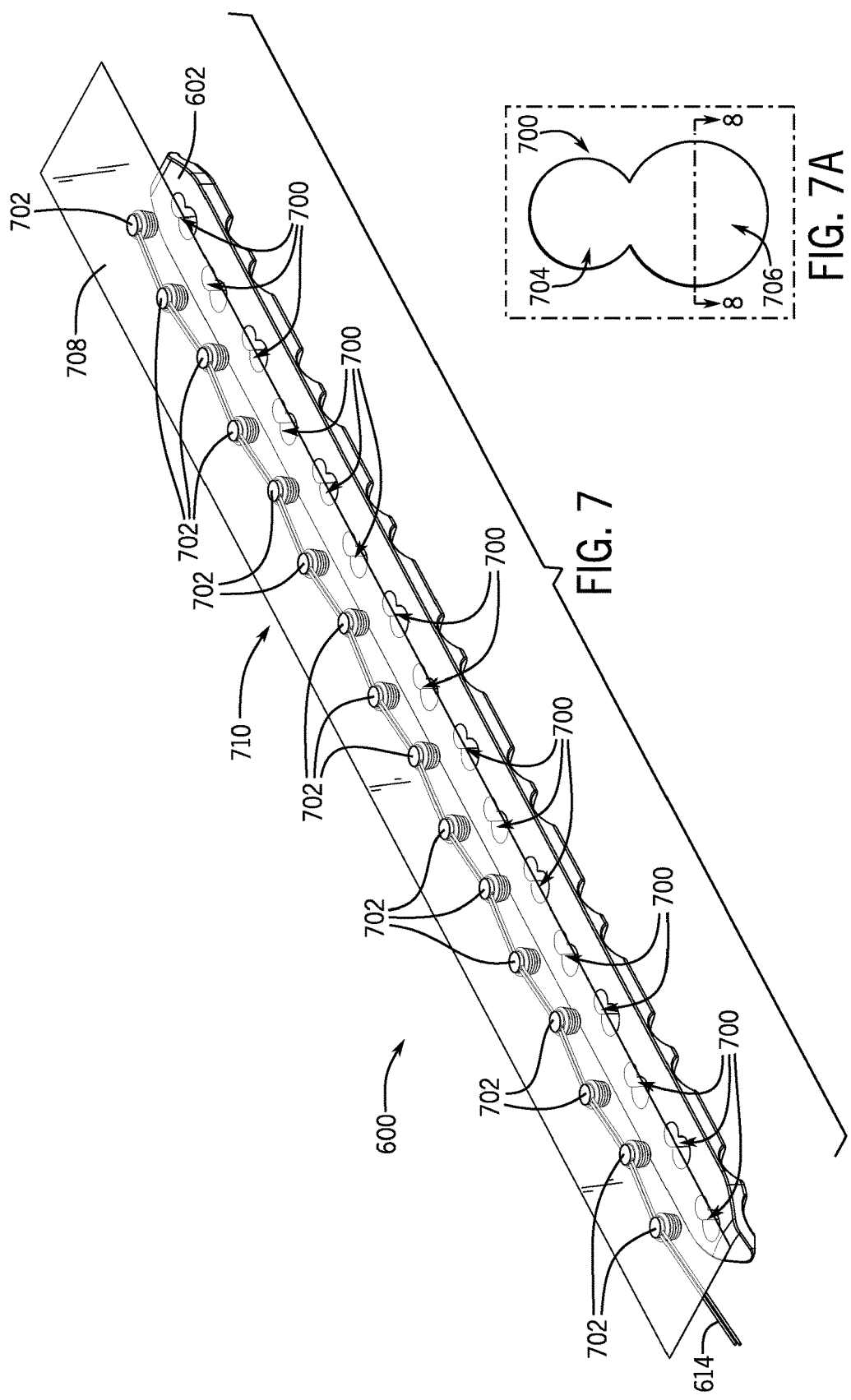
FIG. 7 is a perspective, exploded view of the bone implant of FIG. 6.

FIG. 7 is a perspective, exploded view of the bone implant 600 of FIG. 6. In the illustrated embodiment, the plate 602 includes a plurality of apertures 700. The apertures 700 of FIG. 7 are disposed in a row along a length of the plate 602. In other embodiments, the apertures 700 are disposed in other configurations (e.g., a plurality of rows and/or other configurations). In the illustrated embodiment, the plate 602 includes sixteen of the apertures 700. In other embodiments, the plate 602 includes other numbers of apertures (e.g., 2, 5, 10, 20, or any other suitable number). In the illustrated embodiment, each of the apertures 700 is dimensioned and shaped to receive one of the fasteners 608 of FIG. 6 and one of a plurality of light sources 702.

FIG. 7A is a top view of one of the apertures 700 of FIG. 7. In the embodiment of FIG. 7A, the apertures 700 of FIG. 7 are substantially the same or identical. Therefore, the following description of one of the apertures 700 with reference to FIG. 7A is applicable to the other apertures 700 of FIG. 7. Accordingly, separate descriptions of each of the apertures 700 are not set forth herein. The aperture 700 of FIG. 7A includes a first compartment 704 and a second compartment 706. The first compartment 704 is dimensioned and shaped to receive one of the fasteners 608 of FIG. 6. The second compartment 706 is dimensioned and shaped to receive one of the light sources 702. In other embodiments, instead of having a single aperture to receive both the fastener 608 and the light source 702, the plate 700 may include a first aperture shaped and dimensioned to receive the fastener 608 and a second aperture shaped and dimensioned to receive the light source 702.

Referring again to FIG. 7, the light sources 702 are press-fit or snapped into respective ones of the apertures 700 and, thus, positioned to enable the light sources 702 to emit light through the apertures 700 to the bone 606. In other embodiments, the light sources 702 are coupled to the plate 602 in other ways (e.g., via mechanical fasteners, adhesives, and/or one or more additional and/or alternative ways). In the illustrated embodiment, the light sources 702 are organic light emitting diodes (LEDs) disposed on a strip 708 such as, for example, a transparent film. The light sources 702 and the strip 708 are collectively referred to as an LED strip 710. The light sources 702 may be spaced apart from each other on the strip 708 at distances substantially equal to distances between the apertures 700 to facilitate coupling of the LED strip 710 the plate 602. The light sources 702 are daisy chained (i.e., connected together in series) in the illustrated embodiment.

In some embodiments, the light sources 702 emit near infrared (NIR) light (e.g., light having wavelengths from about 600 nanometers to about 950 nanometers). In some embodiments, the light sources 702 emit light having wavelengths of about 670 nanometers. In some embodiments, the light penetrates the bone 606 by about one-sixteenth of an inch, decreasing osteoblast apoptosis and promoting cell proliferation of the bone 606 to facilitate healing of the bone 606. In some embodiments, each of the light sources 702 has a viewing angle of about 120 degrees to about 170 degrees. In other embodiments, one or more of the light sources 702 has other viewing angles. In some embodiments, each of the light sources 702 has a light coverage of about 100 percent at a distance of about 2 to 3 millimeters outward (i.e., toward the bone 606) from the respective one of the light sources 702. Although the bone implant 600 of FIGS. 6-7A has sixteen light sources, the bone implant 600 can include other numbers of light sources in other embodiments. For example, the bone implant 600 may include one light source, two light sources, five light sources, or other suitable numbers of individual or groups of light sources. In some embodiments, the LED strip 710 generates radiant power exposure of about 200-250 milliwatts per square centimeter (mw/cm$^2$).

Figure 8:
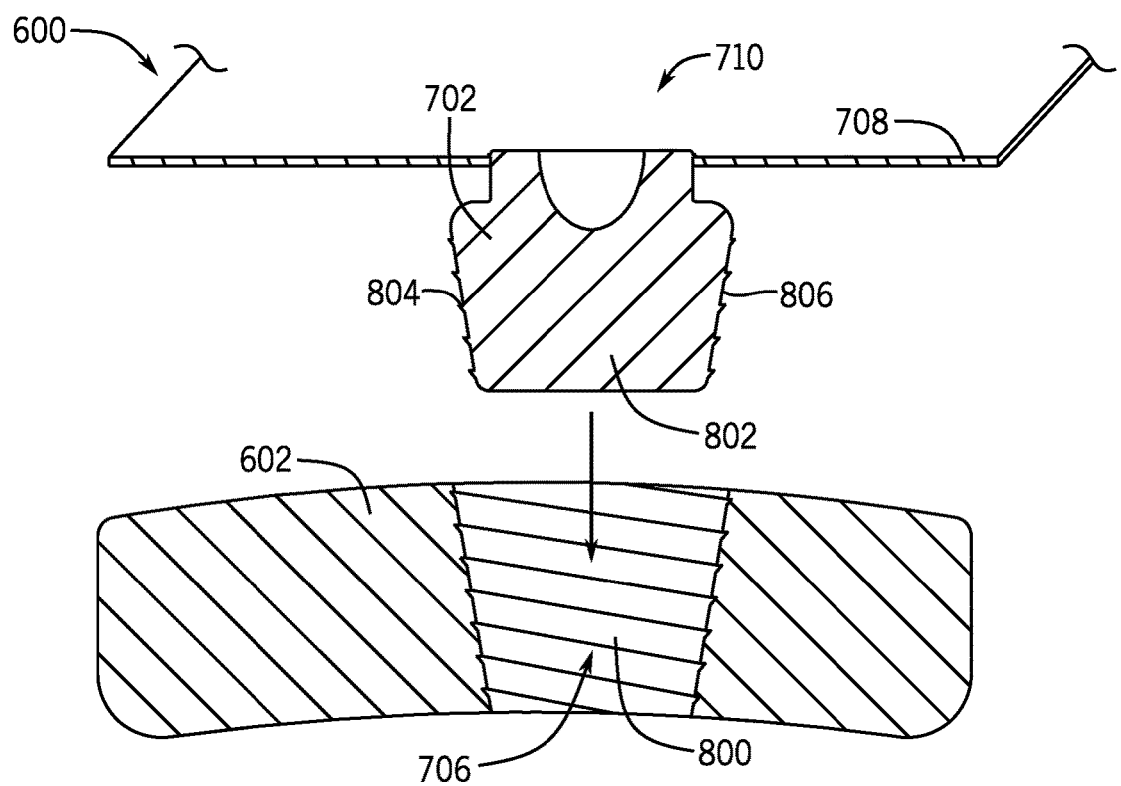
FIG. 8 is a cross-sectional view of the bone implant of FIGS. 6-7A along line 8-8 of FIG. 7A.

FIG. 8 is a cross-sectional view of the plate 602 along line 8-8 of FIG. 7A. In the illustrated embodiment, the second compartment 706 includes grooves or threads 800. The light source 702 includes a housing 802 having a plurality of ribs 804 disposed on a periphery 806 of the housing 802. When the LED strip 710 is coupled to the plate 602, the second compartment 706 receives the housing 802 of the light source 702. As the housing 802 moves into the second compartment 706, the ribs 804 of the light source 702 interact or engage with the threads 800 of the second compartment 706 to secure the light source 702 to the plate 602. Interaction between the ribs 804 and the threads 800 provide tactile feedback to a surgeon or other person coupling the LED strip 710 to the plate 602 that indicates that the light source 702 is secured to the plate 602.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A bone implant in electrical communication with a controller, the bone implant being implanted in a bone of a patient, the bone implant comprising:
   a rod having an aperture extending entirely through the rod, the aperture to receive a fastener to couple the rod to the bone of the patient, the rod and a light source implanted in the bone of the patient;
   the light source disposed on the rod; and
   wherein the controller is in electrical communication with the light source, the controller being configured to execute a program to provide a signal to the light source, the signal causing the light source to emit light onto a portion of the bone adjacent the rod to at least one of stimulate bone growth or reduce bone loss.

2. The bone implant of claim 1, wherein the controller is operatively coupled to the light source via a frangible lead.

3. The bone implant of claim 1, wherein the rod is curved.

4. The bone implant of claim 3, wherein a portion of the light source extends through an end wall defining the channel.

5. The bone implant of claim 1, wherein the rod includes a channel, the light source disposed in the channel.

6. The bone implant of claim 1, wherein the rod includes a passageway extending entirely through the rod along a central, longitudinal axis of the rod.

7. The bone implant of claim 1, wherein the light source is to emit near infrared light.

8. The bone implant of claim 1, wherein the light source is to emit light having wavelengths from about 600 nanometers to about 950 nanometers.

9. The bone implant of claim 1, wherein the signal to the light source is a first signal occurring at a first time period during a first day; and
   wherein the program further includes providing a second signal to the light source during a second time period during a second day, the second signal causing the light source to emit light onto a portion of the bone adjacent the rod to at least one of stimulate bone growth or reduce bone loss.

10. A bone implant implanted in a bone of a patient, the bone implant comprising:
    a rod having an aperture extending entirely through the rod, the aperture to receive a fastener to couple the rod to the bone of the patient;
    a light source disposed on the rod, the light source to emit light onto a portion of the bone of the patient, adjacent the rod to at least one of stimulate bone growth or reduce bone loss;
    a controller operatively coupled to the light source via a frangible lead; and
    wherein the controller is to control power supplied to the light source to enable the bone implant to deliver doses of light of four Joules to six Joules of energy per day.

11. A bone implant, the bone implant being implanted in a bone of a patient, the bone implant comprising:
    a light source to emit light having a wavelength from about 600 nanometers to about 950 nanometers, the light source implanted in the bone of the patient;
    an aperture extending through the bone implant, the aperture to receive a fastener to secure the bone implant to the bone; and
    wherein the light source delivers a predetermined dose of light to the bone of the patient.

12. The bone implant of claim 11, further comprising:
    a controller in electrical communication with the light source; and
    a lead to electronically connect the light source to the controller, the lead having a frangible joint.

13. The bone implant of claim 11, further comprising:
    a controller in electrical communication with the light source and a power source; and
    wherein the controller is configured to execute a program to control power supplied to the light source to enable the light source to deliver a predetermined dose of light to a bone.

* * * * *